(12) United States Patent
Batiste et al.

(10) Patent No.: US 12,667,654 B2
(45) Date of Patent: *Jun. 30, 2026

(54) HEMODIALYSIS ACCESS METHOD FOR A PATIENT

(71) Applicants: Stan Batiste, Granite Bay, CA (US);
Daniel Batiste, Granite Bay, CA (US)

(72) Inventors: Stan Batiste, Granite Bay, CA (US);
Daniel Batiste, Granite Bay, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/458,964

(22) Filed: Jan. 26, 2026

(65) Prior Publication Data

US 2026/0174947 A1 Jun. 25, 2026

Related U.S. Application Data

(60) Continuation of application No. 19/016,373, filed on Jan. 10, 2025, which is a continuation-in-part of application No. 18/202,010, filed on May 25, 2023, now Pat. No. 12,514,968, which is a division of application No. 16/659,386, filed on Oct. 21, 2019, now Pat. No. 12,042,592.

(60) Provisional application No. 62/748,280, filed on Oct. 19, 2018.

(51) Int. Cl.
*A61M 1/36* (2006.01)

(52) U.S. Cl.
CPC ........ *A61M 1/3655* (2013.01); *A61M 1/3661* (2014.02); *A61M 2205/0216* (2013.01); *A61M 2205/3334* (2013.01); *A61M 2206/10* (2013.01)

(58) Field of Classification Search
CPC .............. A61M 1/3655; A61M 1/3661; A61M 2205/0216; A61M 2205/3334; A61M 2206/10; A61M 2206/20; A61F 2250/001; A61F 2250/0039; A61F 2/90; A61F 2002/068; A61F 2250/0071
See application file for complete search history.

(56) References Cited

U.S. PATENT DOCUMENTS

| | | | |
|---|---|---|---|
| 3,826,257 A | 7/1974 | Buselmeier | |
| 4,153,640 A | 5/1979 | Deiner et al. | |
| 4,256,094 A | 3/1981 | Kapp et al. | |
| 4,549,879 A | 10/1985 | Groshong et al. | |
| 4,562,597 A * | 1/1986 | Possis ...................... A61F 2/06 | |
| | | | 128/898 |
| 5,713,859 A | 2/1998 | Finch, Jr. et al. | |

(Continued)

FOREIGN PATENT DOCUMENTS

WO 2009152488 A1 12/2009

*Primary Examiner* — Guy K Townsend
*Assistant Examiner* — Alessandro R Del Priore
(74) *Attorney, Agent, or Firm* — The Powers IP Law Firm

(57) ABSTRACT

An elastic dialysis stent comprises a central restrictor segment located between two tapered segments. The tapered segments are tapered from a larger diameter suitable for joining to tubular graft segments or attaching the stent in a graft or fistula, to the narrower diameter of the elastic central restrictor segment which provides a stenosis. The central restrictor is made of an elastic material which enables the stent to be radially expanded by a balloon catheter to a larger diameter for passage of endovascular devices through the stent for repair of blockages on the venous side of the stent. When the balloon catheter is deflated and removed, the elastic properties of the stent cause it to retract to its original stenotic configuration.

25 Claims, 19 Drawing Sheets

(56)     References Cited

U.S. PATENT DOCUMENTS

| 5,797,879 A | 8/1998 | DeCampli |
| 5,800,514 A | 9/1998 | Nunez et al. |
| 5,849,036 A | 12/1998 | Zarate |
| 6,045,496 A | 4/2000 | Pacella et al. |
| 6,056,717 A | 5/2000 | Finch et al. |
| 6,146,414 A | 11/2000 | Gelman |
| 6,261,257 B1 | 7/2001 | Uflacker et al. |
| 6,338,724 B1 | 1/2002 | Dossa |
| 6,371,981 B1 | 4/2002 | Yang et al. |
| 6,461,321 B1 | 10/2002 | Quinn |
| 6,585,762 B1 | 7/2003 | Stanish |
| 6,598,278 B2 | 7/2003 | Chen et al. |
| 7,025,741 B2 | 4/2006 | Cull |
| 7,108,673 B1 | 9/2006 | Batiste |
| 7,540,859 B2 | 6/2009 | Claude et al. |
| 7,811,298 B2 | 10/2010 | Birk |
| 7,833,186 B1 | 11/2010 | Batiste |
| 8,096,967 B2 | 1/2012 | Radoicic |
| 8,216,174 B2 | 7/2012 | Wilk et al. |
| 8,551,033 B1 | 10/2013 | Batiste |
| 8,684,960 B2 | 4/2014 | Batiste et al. |
| 8,715,218 B2 | 5/2014 | Batiste et al. |
| 9,907,900 B1 | 3/2018 | Batiste et al. |
| 2003/0114918 A1 | 6/2003 | Garrison et al. |
| 2004/0249334 A1 | 12/2004 | Cull |
| 2006/0095114 A1 | 5/2006 | Hartley et al. |
| 2006/0224100 A1 | 10/2006 | Gertner |
| 2006/0229548 A1 | 10/2006 | Cull |
| 2007/0142907 A1 | 6/2007 | Moaddeb et al. |
| 2011/0015723 A1 | 1/2011 | Batiste et al. |
| 2011/0125244 A1 | 5/2011 | Roeder et al. |
| 2011/0172692 A1* | 7/2011 | Wu .................... A61M 1/3655 |
| | | 606/191 |
| 2018/0078366 A1 | 3/2018 | Sievers et al. |
| 2019/0125517 A1* | 5/2019 | Cully ...................... A61F 2/07 |
| 2020/0155751 A1 | 5/2020 | Batiste |
| 2023/0201014 A1 | 6/2023 | Sirhan et al. |

* cited by examiner

FIG. 1
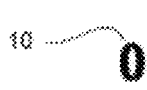
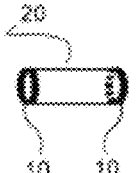
FIG. 2A
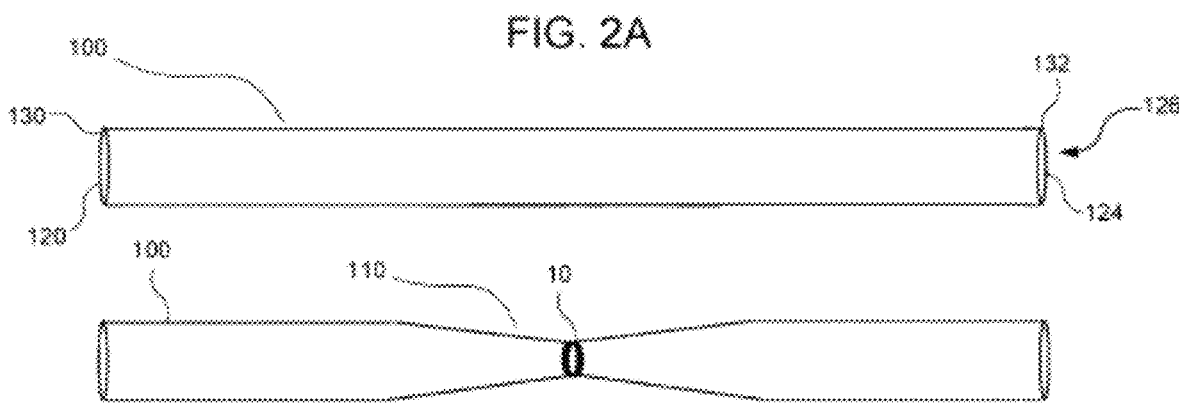
FIG. 2B
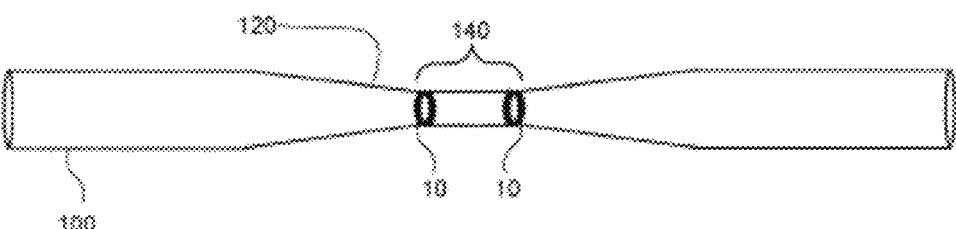
FIG. 2C

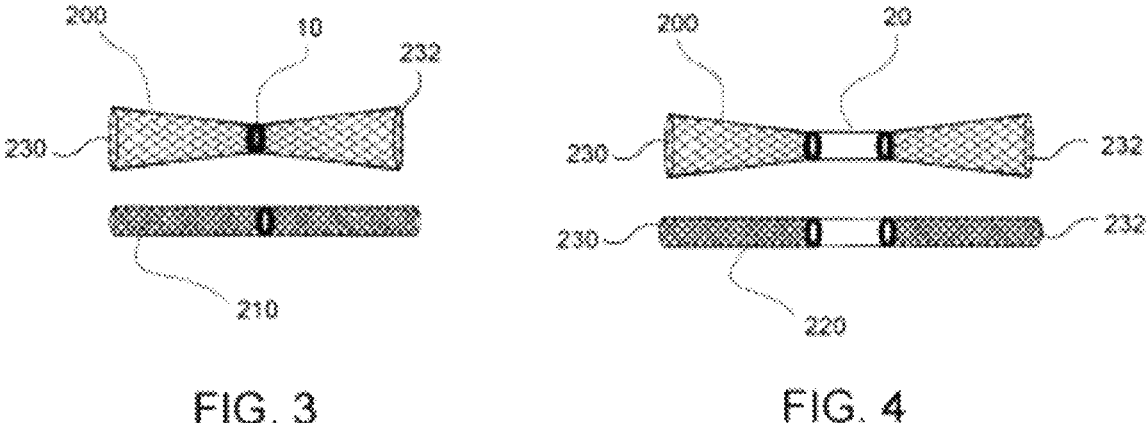
FIG. 3                                        FIG. 4
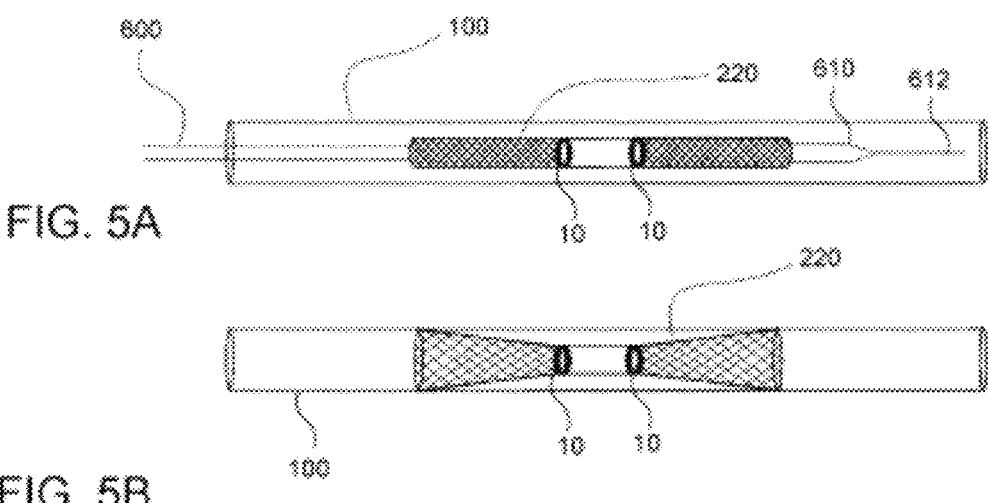
FIG. 5A
FIG. 5B

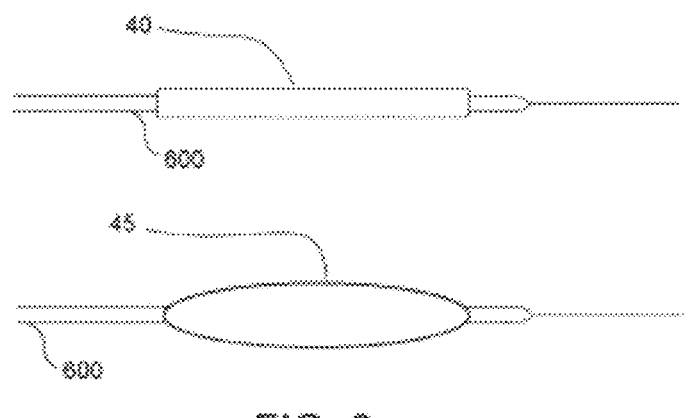
FIG. 6
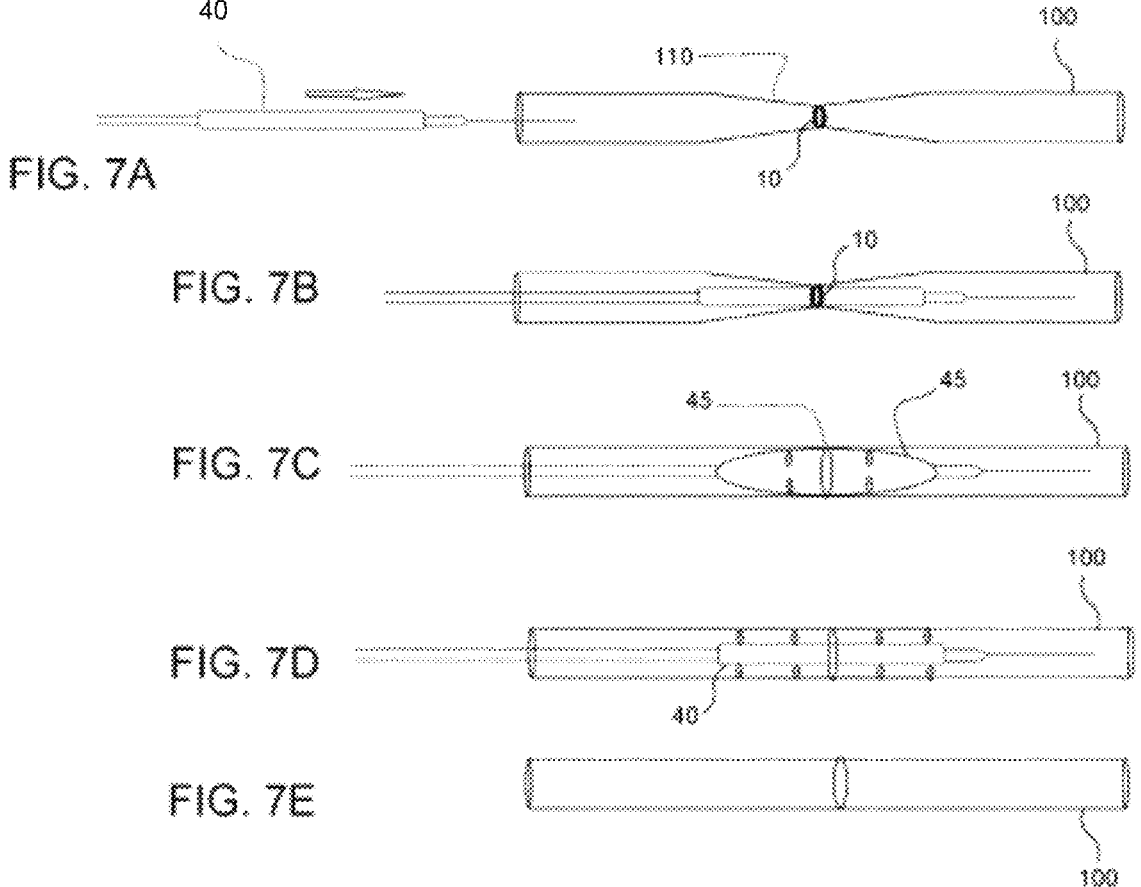
FIG. 7A
FIG. 7B
FIG. 7C
FIG. 7D
FIG. 7E

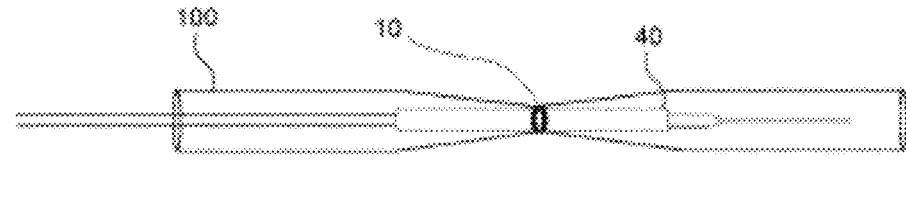
FIG. 9A
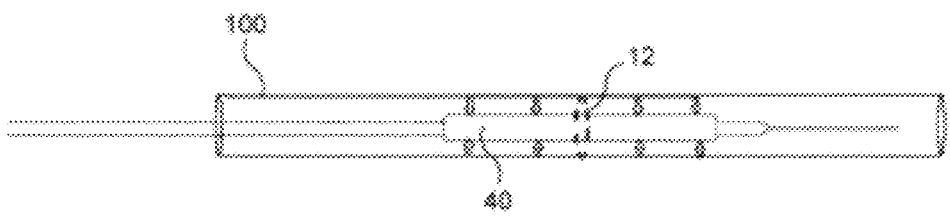
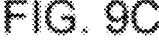
FIG. 9B
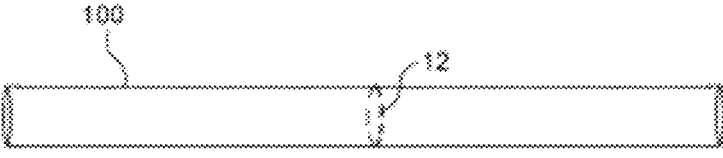
FIG. 9C
FIG. 9D

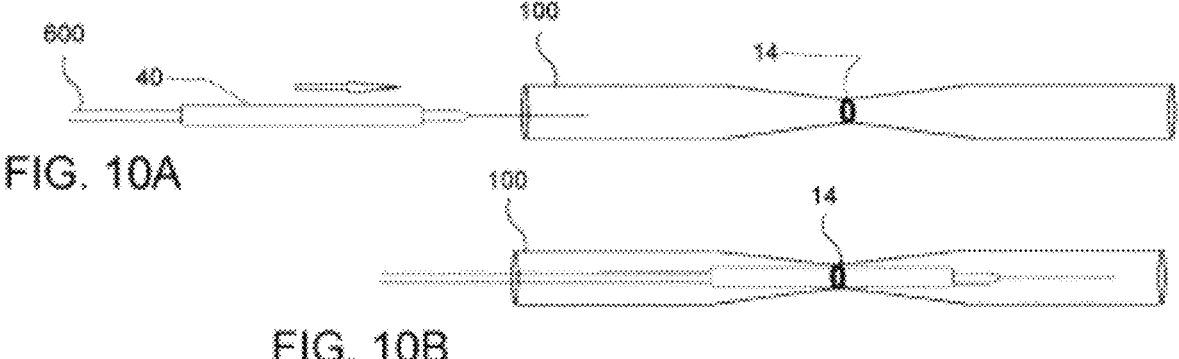
FIG. 10A
FIG. 10B
FIG. 10C
FIG. 10D
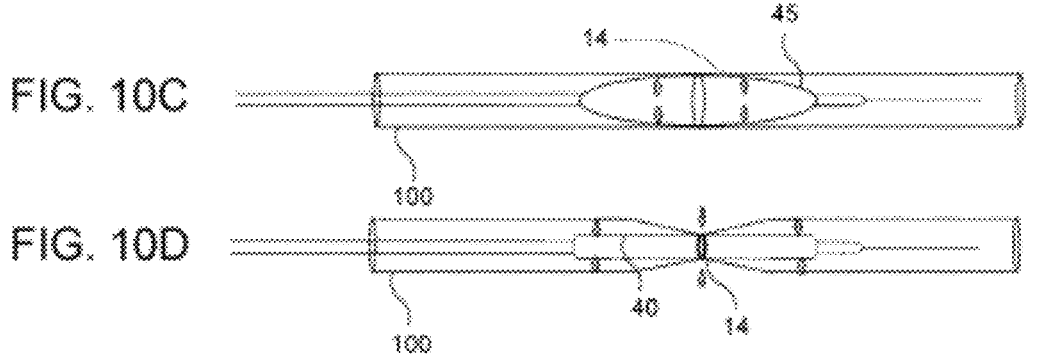
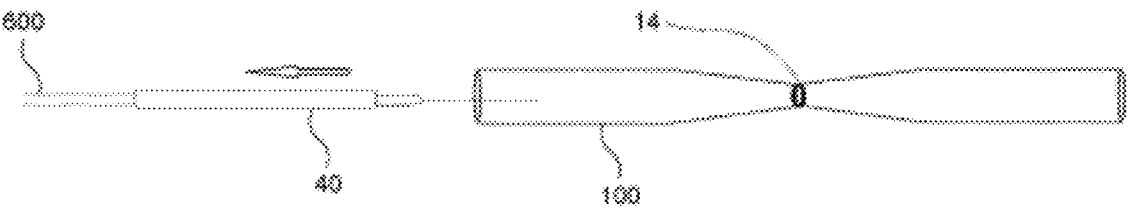
FIG. 10E

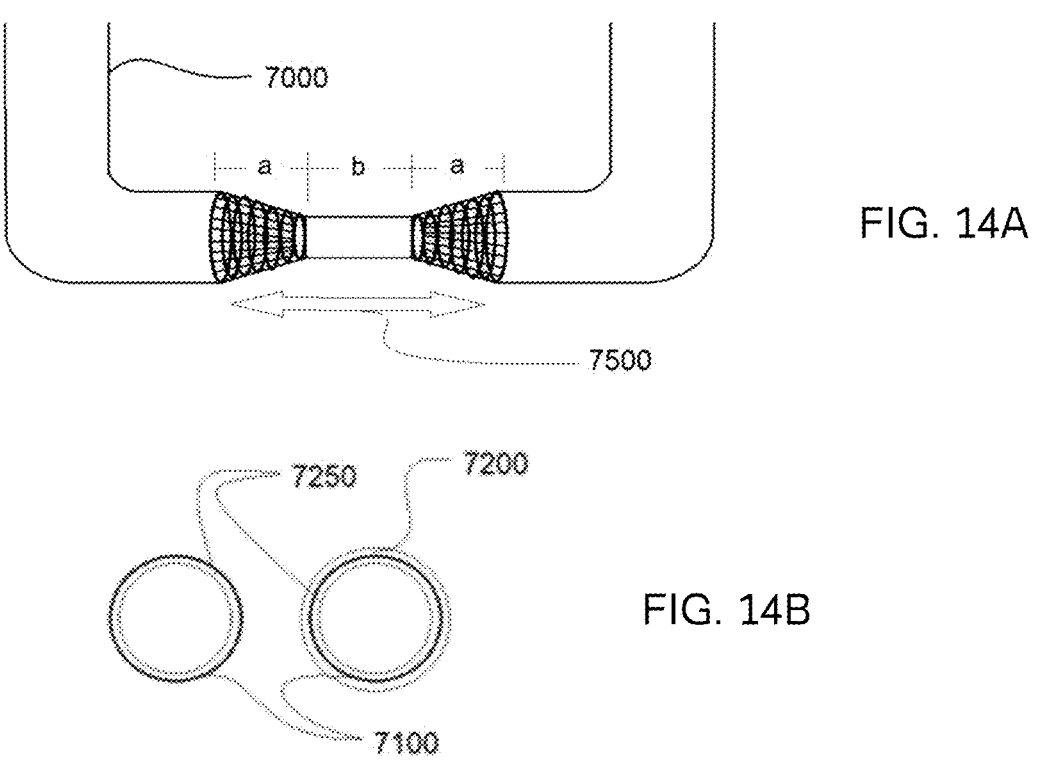
FIG. 14A
FIG. 14B
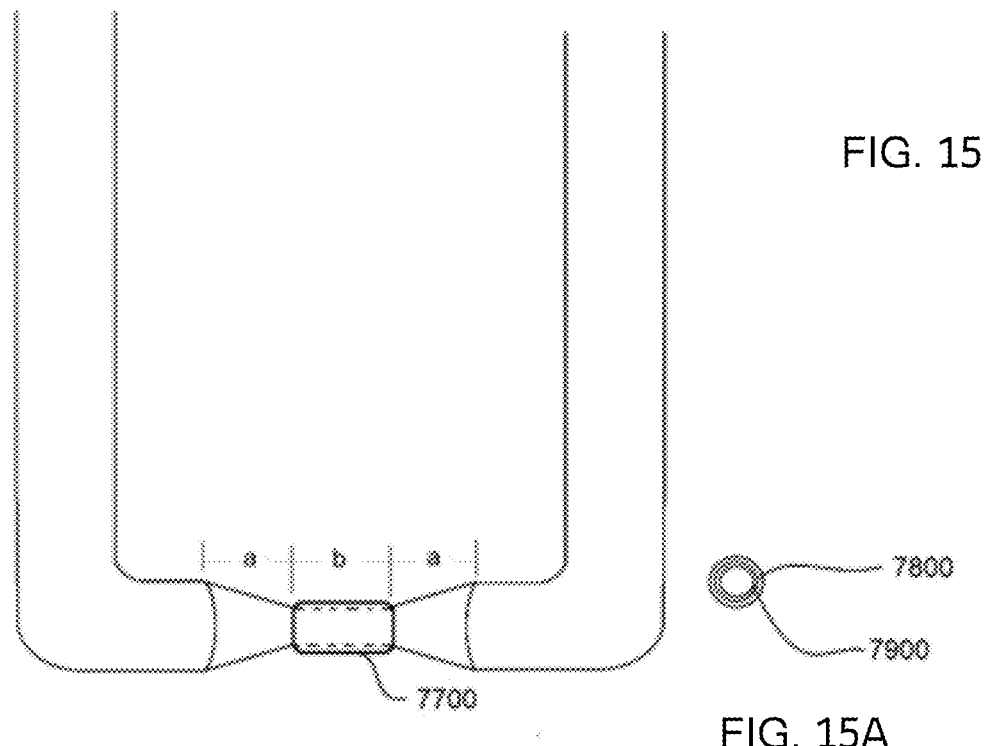
FIG. 15
FIG. 15A

HEMODIALYSIS ACCESS METHOD FOR A PATIENT

CROSS-REFERENCE TO RELATED APPLICATIONS

This application is a continuation of U.S. patent application Ser. No. 19/016,373, filed Jan. 10, 2025, which is a continuation-in-part of U.S. patent application Ser. No. 18/202,010, filed May 25, 2023, now U.S. Pat. No. 12,514, 968, which is a division of U.S. patent application Ser. No. 16/659,386, filed Oct. 21, 2019, now U.S. Pat. No. 12,042, 592, which claims the benefit of U.S. provisional application No. 62/748,280, filed Oct. 19, 2018.

FIELD OF THE INVENTION

This invention relates generally to arterial venous grafts and shunts for dialysis and in particular to arteriovenous (AV) grafts and shunts with resilient (e.g., elastic) flow restrictors created to modify the flow dynamics through the graft.

BACKGROUND OF THE INVENTION

There are currently more than 400,000 patients in the United States with end-stage renal disease (ESRD) and many times more throughout the world. Patients with ESRD have lost their normal kidney function and as a result require dialysis to substitute the function of the kidney cleansing the blood.

The challenge with providing hemodialysis is maintaining access to large volumes of blood when our bodies constantly fight medical attempts to keep dialysis access available. Currently there are three ways to provide hemodialysis: dialysis catheters, arterial venous fistulas, and arterial venous grafts. All current methods are, however, limited, providing access for only short periods of time before the body begins to occlude vessels and impede vascular access. This requires patients to have repeated invasive procedures repair or replace the means for vascular access. Additionally, in the case of AV shunt configurations used to provide access for dialysis, blood flow is shunted away from the hand and there is a continuous loss of arterial blood flow. This can lead to unwanted medical consequences including finger necrosis and excessive heart action. To overcome these drawbacks, an implementation of the present invention extends the life of the dialysis graft as well as decreasing the loss of blood to the extremity while also maintaining efficient use of the cardiac output, thus prolonging the lives of patients.

SUMMARY

Arteriovenous fistulas and grafts termed AV shunts are the most effective means to provide large volume blood access for hemodialysis patients. Patency rates however are relatively low as both means of AV shunts occlude primarily due to the occurrence of normal vein stenosis at the output of the graft. This is a result of high pressure at the venous output of the shunt, pulsation and high flow rates. As mentioned above, an additional limitation of current AV shunts is the stealing of blood from the artery that would normally feed the distal portion of the extremity, such as the finger. Blood flow is shunted through the AV fistula back to the heart, thus bypassing the lower portion of the extremity. This creates two issues, the first being the distal extremity ischemia that often results in finger necrosis and resultant loss. The other is the constant loss of cardiac output, making the heart continuously work much harder than it normally would without a shunt. One proposal to surgically treat these problems is to create a vascular band around the fistula or graft, thereby creating a surgical flow restrictor. Another method described in prior designs of one of the present inventors is a manufactured flow restrictor within the body of the graft or fistula. Other one of these designs describe several such devices including preformed restrictor, balloon restrictors and restrictors using cellular materials among several others. U.S. Pat. No. 8,715,218 (Batiste) entitled Self Adjusting Venous Equalizing Graft and Endothelial Lining Therefore is incorporated by reference in its entirety herein.

One implementation of the present invention provides an innovative means to create a flow restrictor within an AV shunt that can be modified if hemodynamics or patient clinical condition changes. This design utilizes a mechanical band that functions to selectively and controllably restrict the inner diameter of the AV shunt. The innovative band may contain several different properties, including a pliable design that can be stretched with a balloon and remains expanded, completely eliminating the stenosis. Another implementation includes a fracturable band which breaks at predetermined sites in order to release the flow restriction. The expandable or fracturable flow restrictors can be placed prior to shunt surgical placement or via percutaneous endovascular placement as described herein. All of these designs enable the stenotic restriction of the stent to be eliminated when the patient's medical condition warrant.

As mentioned above, methods of providing vascular access for dialysis are subject to the response of bodily functions to intrusions into the vascular system, including normal physiologic defenses to man-made materials and structures. In particular, plaque buildup and clotting can develop at the venous output of the shunt due to the abnormal blood pressures and flow rates created in the vein by the shunt. It has been found that there is only 50% shunt patency at one year and less than 25% at two years. Once occluded, the shunt becomes full of blood which is static, which subsequently becomes thrombus. In this state, the shunt is no longer suitable for dialysis access. A viable technique for dealing with such occlusions in other regions of the vasculature is angioplasty, which is well developed for treating occlusions in normal blood vessels. It is an object of the present invention to provide a device and method for enabling angioplasty or similar procedure in an arteriovenous fistula or graft having a stenotic region. Numerous designs for grafts and fistulas for dialysis access have been proposed in the prior art, but none to our knowledge have facilitated repair or remediation of an occluding stent or vessel. U.S. Pat. No. 4,562,597 (Possis et al.), for example, describes a vascular graft for supplying a flow of blood to coronary arteries. The Possis graft is a tube with a blood flow restrictor in the tube in the form of a clamp, which can be adjusted to determine the blood flow through the graft. No consideration is given to occlusion of the graft or to remedying such occlusion. U.S. Pat. No. 11,229,512 (Cully et al.) describes a transjugular intrahepatic portosystemic shunt for connecting the portal vein to the inferior vena caba by way of the hepatic vein. The shunt includes a controlled expansion element which diametrically constrains and limits expansion of the endoprosthesis. Following deployment of the shunt, the endoprosthesis can be further expanded by means of balloon dilation so that it will exhibit and maintain a desired diameter and flow rate. No mention is made of possible occlusion of the shunt or its remediation.

In accordance with the principals of the present invention, an AV graft is provided with a stenotic region which reduces the blood flow through the graft. The stenotic region is formed of an elastic material which maintains the passageway of the stenotic region at a first, reduced size. The stenotic region, being elastic, can be expanded to a second, enlarged size. Such expansion is caused by mechanical means applying pressure radially outward, such as a balloon catheter. When the balloon catheter passes through the AV graft from the arterial side to the vascular side of the stenosis, the enlargement of the elastic stenosis enables a catheter for angioplasty to pass through the stenotic region and access and treat occlusions on the vascular side of the stenosis and in the vein to which the AV graft is attached. The elastic design of the stenosis enables it to reform to the original flow restrictor configuration once the balloon therapy is concluded. By enabling such maintenance to be performed on the AV graft and its attached vessels, the patency life of the AV graft is extended. In one implementation the elastic stenosis is provided in a polymeric AV graft. In another implementation the elastic stenosis is provided as a deployable stent which can be placed in an arteriovenous fistula or graft.

In a preferred implementation, an elastic dialysis stent comprises an elastic central restrictor segment having a central lumen and first and second ends, the central lumen exhibiting a stenotic inner diameter when not subject to radially expansive pressure. First and second tapered segments having central lumens extend from the ends of the elastic central restrictor segment, the tapered segments having ends remote from the elastic central restrictor segment which exhibit greater diameters than the stenotic inner diameter of the elastic central restrictor segment. The tapered segments are adapted to move radially in concert with movement of the ends of the elastic central restrictor segment to which they are attached. The elastic central restrictor segment is further adapted to elastically expand radially when radially expansive pressure is applied in the central lumen of the elastic central restrictor segment, and to elastically contract to its stenotic inner diameter when the radially expansive pressure is removed. Disclosed herein is a shunt having a flexible tube which has a first and second end, and a central opening with a first diameter extending from the first to the second end. The flexible tube has one or more restrictor bands which have a second diameter around the flexible tube. The restrictor band is located between the first and second end of the flexible tube, and the second diameter is less than the flexible tube's first diameter.

In one embodiment the shunt described above is an arterial venous shunt (AV shunt) which may be configured to have a restrictor band that expands between a first and a second position. The restrictor band may include sections that are configured to fracture (i.e., fracturable sections) in response to outward pressure thereby increasing a diameter of the one or more restrictor bands to a diameter greater than the second diameter. In one or more embodiments, the one or more restrictor bands in the AV shunt have at least two different inner diameters.

The tube length of the AV shunt has an inlet end, an outlet end, and a central opening which extends from the inlet to the outlet ends such that central opening has a first diameter. In this embodiment, at least one band extends around a portion of the tube length and is located between the ends. The bands create a reduced diameter section of a second diameter that is adjustable from the second diameter, which is less than the first diameter to a third diameter which is greater than the second diameter. The third diameter of the AV shunt may be the same as the first diameter.

The band of the AV shunt may be further expandable from the third diameter to a fourth diameter, the fourth diameter being greater than the third diameter. In some embodiments, the band also has sections which are configured to fracture in response to outward pressure thereby increasing the band from the second diameter to the third diameter and may further contain two or more restrictor bands of at least two different inner diameters.

In one configuration, the tube functioning as an AV shunt has a central opening with a first diameter extending from both the inlet and outlet ends. In one embodiment, the at least one band has a second diameter which extends around the tube and is located between the inlet end and the outlet end, that creates a reduced diameter section in the tube such that the band is configured to expand in response to outward pressure and increase its diameter to adjust from the second diameter to a third diameter and then maintain the third diameter after the outward pressure is removed from the band. The amount of increase in diameter of the band is responsive to an amount of outward pressure. The band may be manufactured from elastic material which does not return to its original shape when expanded. In this embodiment, the inlet end of the AV shunt is configured to be connected to an artery, while the outlet end is configured to be connected to a vein. In other embodiments, multiple bands made from a fractionable material having differing diameters are arranged on one tube and consist of two sets of opposing mirrored sets of bands.

BRIEF DESCRIPTION OF THE DRAWINGS

FIG. 1 is an illustration of a short flow restrictor and long flow restrictor.

FIGS. 2A, 2B, and 2C are a linear section of an AV graft (tube) and grafts with flow restrictors applied.

FIG. 3 is a short flow restrictor on a stent expanded and collapsed.

FIG. 4 is a long flow restrictor on a stent expanded and collapsed.

FIGS. 5A and 5B are a stent deployment catheter with collapsed stent and deployed stent.

FIG. 6 is a collapsed (unexpanded) and expanded balloons.

FIG. 7A is an illustration of a collapsed balloon advancing into graft with short restrictor.

FIG. 7B is an illustration of a balloon positioned within the short restrictor.

FIG. 7C is an illustration of balloon inflated expanding restrictor.

FIG. 7D is an illustration of balloon deflated.

FIG. 7E is an illustration of balloon removed and expanded flow restrictor.

FIG. 9A is an illustration of a deflated balloon within flow restrictor.

FIG. 9B is an illustration of an expanded balloon and fractured, expanded flow restrictor 10a.

FIG. 9C is an illustration of a balloon deflated and expanded, fractured restrictor.

FIG. 9D is an illustration of a graft with expanded, fractured restrictor.

FIG. 10A is an illustration of a deflated balloon advancing into flow restrictor.

FIG. 10B is an illustration of a deflated balloon within flow restrictor.

FIG. 10C is an illustration of a balloon expanded within flow restrictor.

FIG. 10D is an illustration of a balloon deflated and elastic restrictor.

FIG. 10E is an illustration of balloon removal and elastic restrictor regaining shape.

Figure 11:
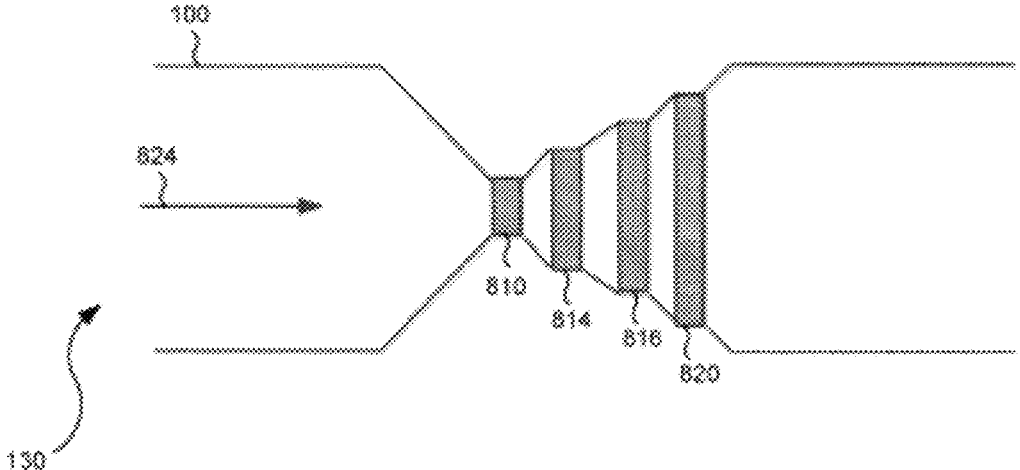

FIG. 11 illustrates one such embodiment that includes a stent tube having multiple bands of various diameters.

Figure 12:
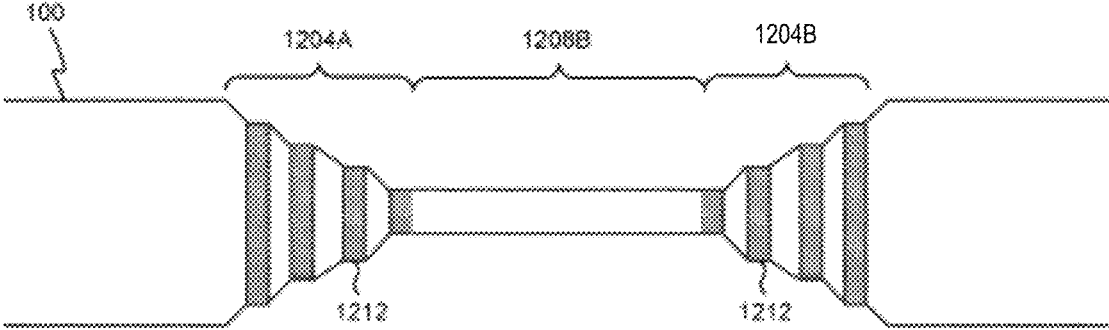

FIG. 12 illustrates an embodiment with a mirror set of bands.

Figure 13:
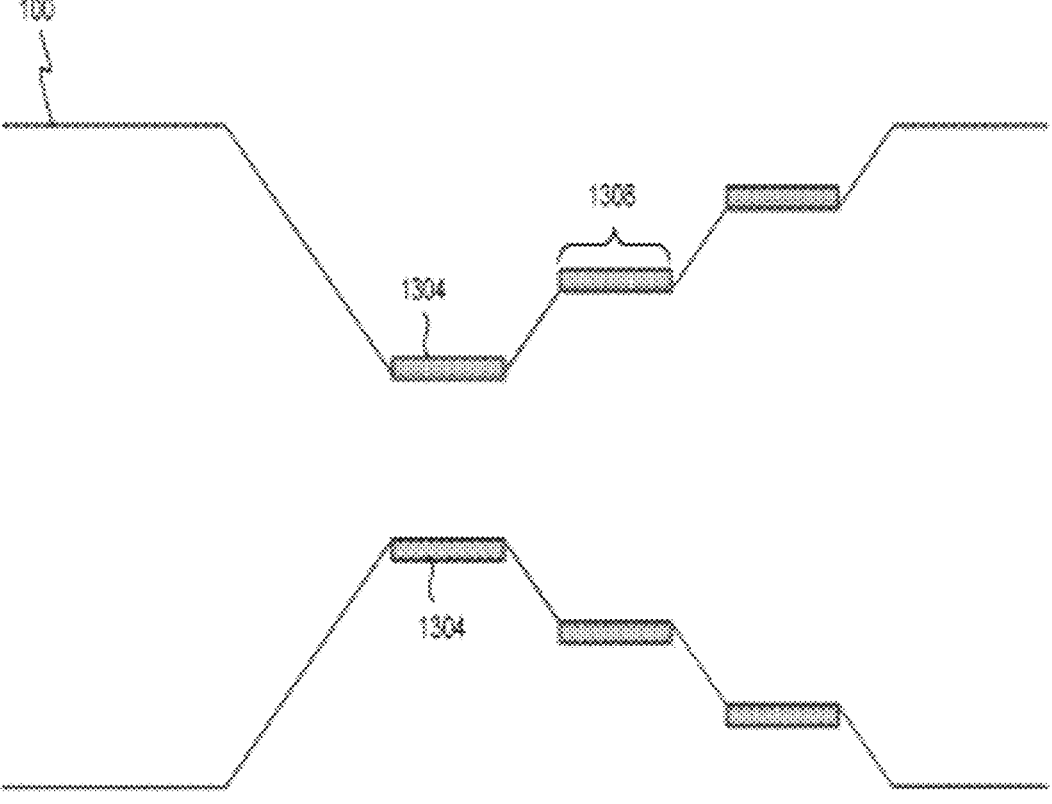

FIG. 13 illustrates an embodiment with bands having a greater width.

FIG. 14A illustrates a graft with an elastic flow restrictor unit comprising tapered segments and an elastic restrictor segment.

FIG. 14B illustrates cross-sectional views of two implementations of the graft of FIG. 14A.

FIG. 15 illustrates a graft with the elastic restrictor unit comprising an elastic band.

FIG. 15A illustrates the graft and elastic band of FIG. 15 in cross-section.

FIG. 16A-16K illustrate an endovascular guidewire introduced into a graft, an uninflated balloon being advanced over the guidewire, the balloon after having been advanced until it opposes a blood clot, the balloon being inflated by standard hydrodynamic means, the balloon being deflated, the balloon expanding an elastic flow restrictor, the elastic flow restrictor returned to its original configuration, the balloon partially inflated, the balloon inflated within a graft, the balloon deflated and advanced through the graft until it opposes a clot, and the balloon inflated to compress buildup on a wall of a graft, respectively.

Figure 17A:
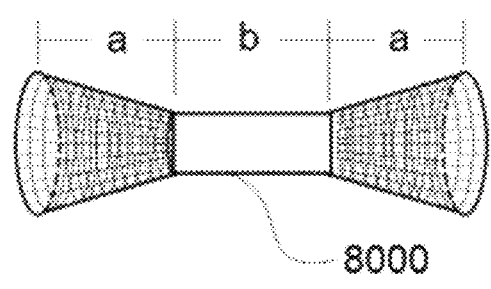
Figure 17B:
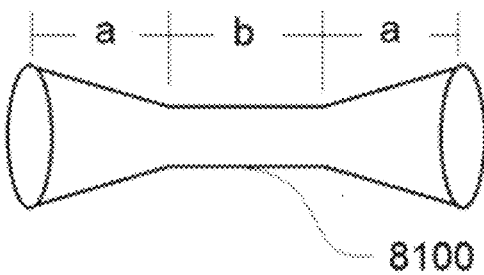

FIGS. 17A and 17B illustrate two implementations of a deployable elastic stent of the present invention.

Figure 18A:
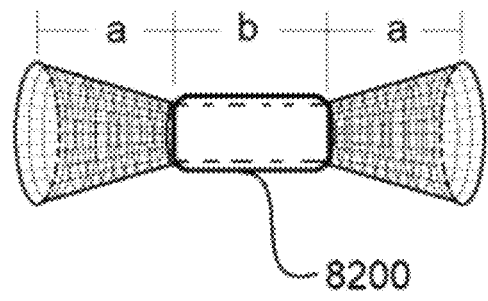
Figure 18B:
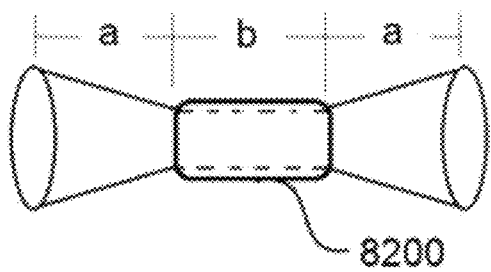

FIGS. 18A and 18B illustrate two implementations of a deployable elastic stent of the present invention in which the stenotic region comprises an elastic band.

Figure 19:
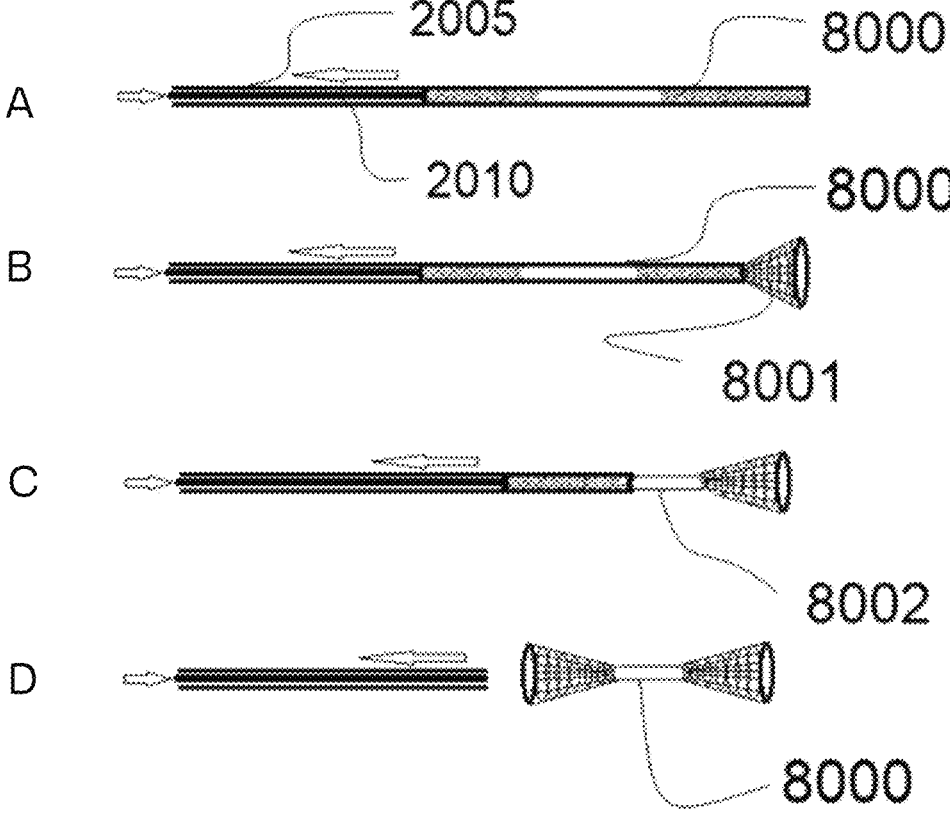

FIG. 19 illustrates a deployable stent of the present invention being deployed by an endovascular catheter.

Figure 20:
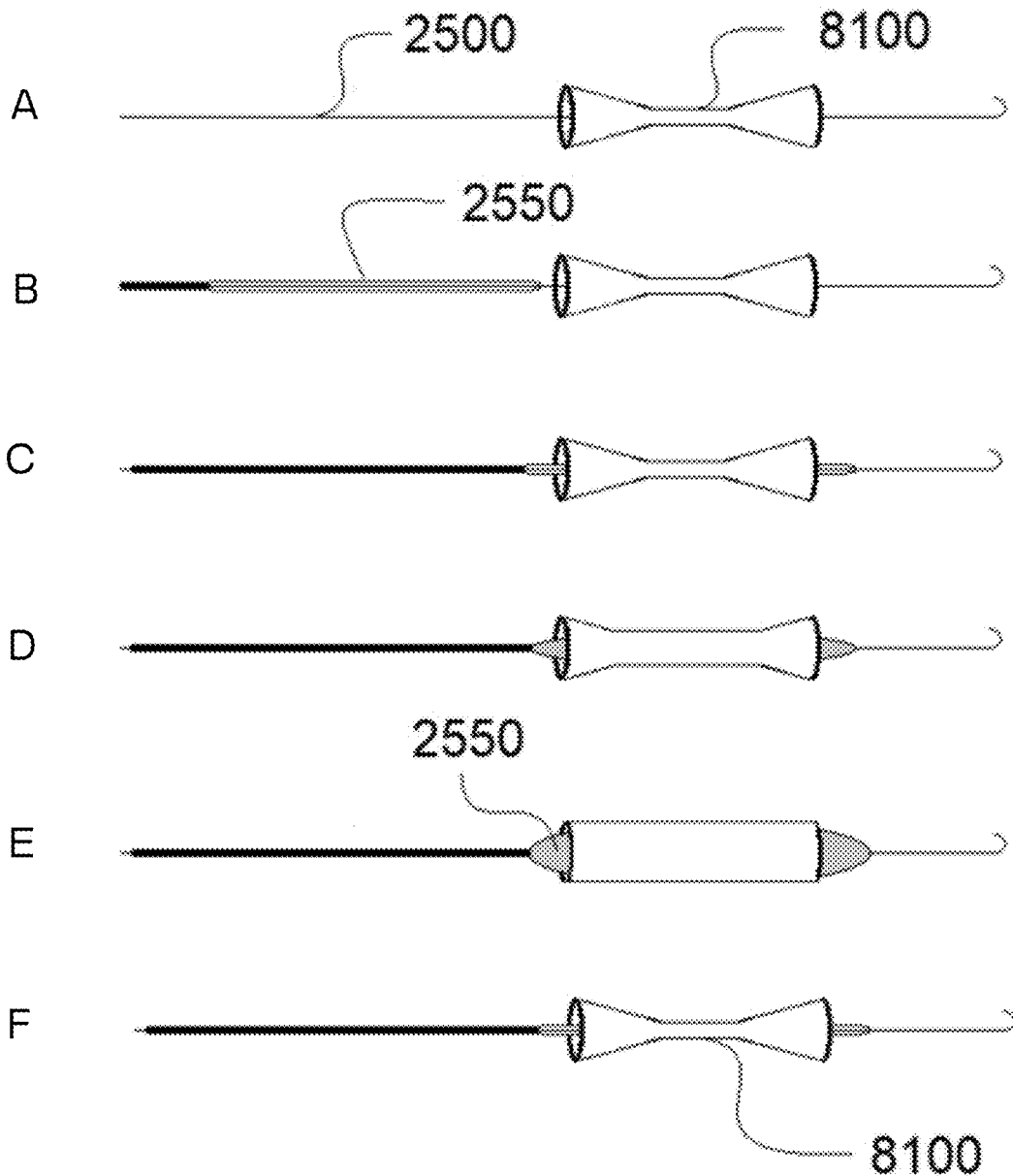

FIG. 20 illustrates an elastic stent of the present invention being dilated by a balloon catheter.

Figure 21:
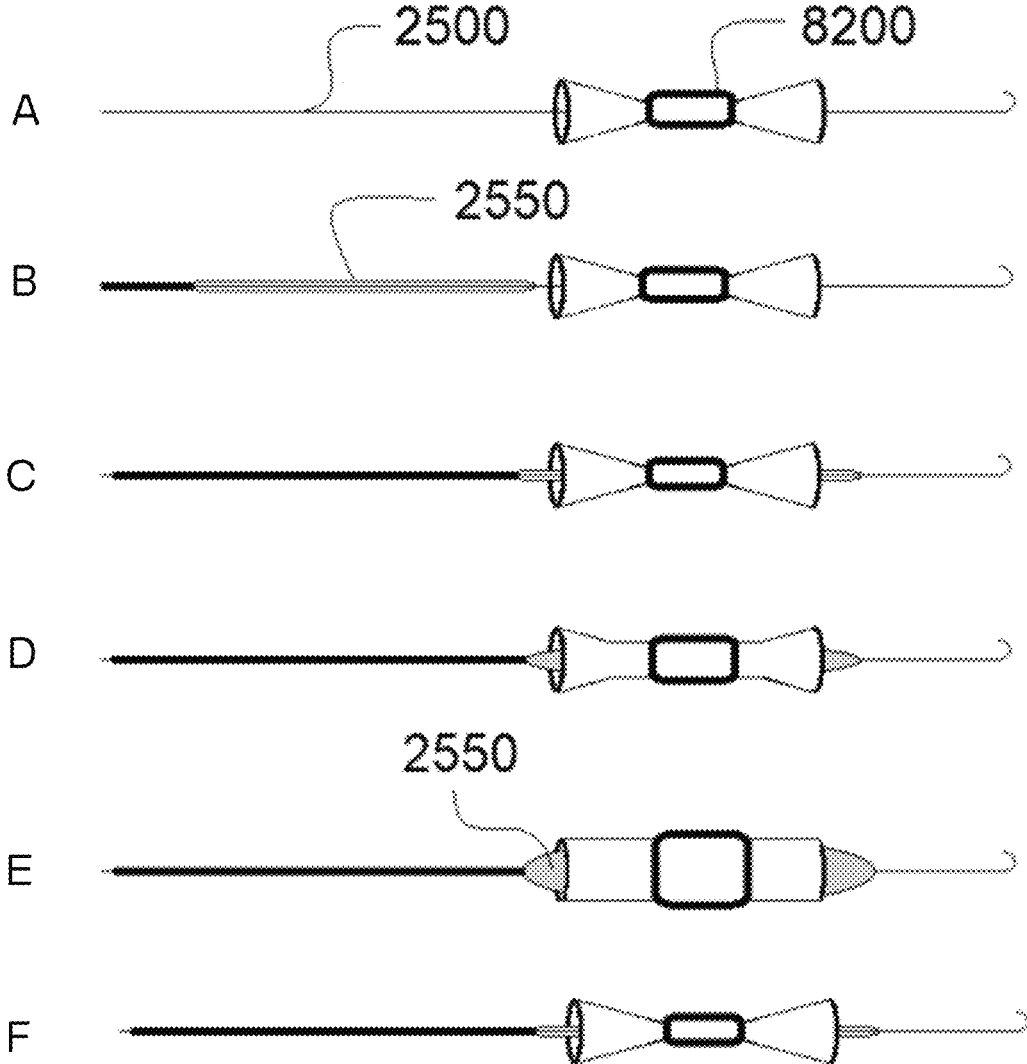

FIG. 21 illustrates a deployable stent of the present invention with an elastic band being dilated by a balloon catheter.

DETAILED DESCRIPTION OF THE PREFERRED EMBODIMENTS

As employed herein, the term "coupled" shall mean connected together either directly or via one or more intermediate parts or components.

As employed herein, the term "number" shall mean one or an integer greater than one (i.e., a plurality).

In one or more embodiments the invention utilizes a band to create external pressure on elements in order to narrow the inner lumen of a dialysis shunt thereby creating a stenosis that acts as a flow restrictor. The restricted flow then creates hemodynamic conditions within the shunt which help eliminate shunt failure and improve flow to the extremities while decreasing cardiac output. As shown in FIG. 1 there are two sizes of bands or restrictor length represented, short (10) and long (20). Bands of different sizes may be used, such as wider versions shown in FIG. 13. It is also contemplated that that the long restrictor length may be formed by two bands 10, one at each end of the narrowed restrictor area, or multiple bands spaced for form the narrowing. The restrictor bands can be composed of materials that have the properties of expandable, fracturable and elastic. In one embodiment the restrictor is able to be expanded in diameter and also be reduced in diameter.

FIG. 2A illustrates an example tube 100 that may be used to form the shunt. The term shunt and graft may be used interchangeably herein. The tube 100 has an outer wall and an inner opening 126 that extends through the tube. The tube has an inlet end 130 (first end) that receives blood flow and an outlet end 132 (second end) that is for an outflow of blood. The tube 100 may be of different diameters to match the diameter of a vessel to which the tube will connect. It is contemplated that in one embodiment the inlet end is configured to connect to an artery while the outlet end is configured to connect a vein. The tube 100 may be any length and may be trimmed to cut to a suitable length. It is also contemplated that bands 10 may be manufactured with bands on the tube 100 or the bands may be placed on the tube at the desired location just prior to or during a medical procedure.

FIG. 2B illustrates the restrictor band 10 deployed on the outside of the hollow member (tube 100) of the arterial venous graft that is surgically placed within a patient. Once placed in a patient, blood flow through the graft will be limited due to the restriction 110, thereby improving conditions for graft patency while maintaining the ability to have dialysis. The conditions that are improved include, but are not limited to, a reduction or elimination of normal vein stenosis at the output of the graft and stealing of blood from the artery.

FIG. 2C illustrates an embodiment with two bands 10 on the tube 100 to create a longer restricted region 140. One or more additional bands may be placed in the restricted region 140 to maintain the narrowing of the restricted region.

FIG. 3 illustrates an endovascular stent with a restrictor band. The stent 200 is shown in a contracted and expanded position. As shown, the stent 200 is provided with a restrictor band 10. The stent 200 has a first end 230 and a second end 232 and is configured to be placed inside a blood vessel of a patient. The short flow restrictor 10 on a stent expanded (200) and collapsed (210) is shown. Endovascular stents are understood by those of ordinary skill in the art and as such they are not described in detail herein. The restrictor band in the stent 200 serves the same purpose as when used in connection with a shunt.

FIG. 4 illustrates the restricted section 20 placed on the outside portion of an endovascular stent 200 both in the collapsed position (bottom) and the deployed expanded position (top). As with FIG. 3, the method of placement is similar to traditional stent placement where percutaneous access is first gained, followed by wire access, followed by collapsed stent advancement to the desired location in the vessel. Once positioned, the stent 200 is deployed. With the restrictor bands 10, 20 in place, the outer portions of the stent (ends 230, 232) will open to oppose the vessel wall. The restrictor 10, 20 located in the middle, or between the ends, or away from the ends, will create radial pressure within the central portion of the stent, prohibiting its central expansion, thereby creating a restriction. This restrictor will maintain a narrowing, creating the desired hemodynamic effects.

FIGS. 5A and 5B illustrates a stent deployment catheter 600 with collapsed stent 220 and deployed stent. This is but one possible system for deployment. The catheter 600 is placed inside the vessel and advances to the deployment location. The stent 220 includes the bands 10 which form the restriction. The catheter is inserted into a vessel or a shunt tube 100 and the stent 220 positioned to a location at which the stent will be placed. Element 100 may be a shunt tube or a vessel of a patient. In this embodiment, the stent 220 is secured to a balloon 610 which is guided by a wire 612. When the balloon is expanded, as shown in FIG. 5B, the stent 220 is secured to the wall of the vessel to maintain itself in place. The outer ends of the stent 220 expand while the restricted portion between the bands 10 does not expand and thus forms the restricted section. The center area of the balloon 610 may not expand thus leaving the narrow area between the bands un-expanded.

FIG. 6 illustrates an unexpanded balloon 40 in connection with a catheter 600 and an expanded balloon 45 in connection with a catheter 600. Catheter-based balloons are understood by those of ordinary skill in the art and as such are not described in detail herein.

Once created or deployed, various clinical situations may dictate modification of the restrictor whether permanent or temporary. The modification may include the diameter of the restriction or the length of the restricted section. Thus, the design anticipates the need to alter the restrictor once placed. The restrictor bands 10 may be altered with various materials depending on the clinical situation and hence the restrictors bands may be expandable, fracturable or elastic. In some embodiments, the restrictor bands 10 return, or can be manipulated to return, to a narrower diameter after being expanded.

As shown in FIGS. 7A through 7E, the expandable restrictor is described where the non-expanded restrictor band 10 is first used within the shunt (FIG. 7A) to create a restricted section 110 in the shunt tube 100. When clinically needed, a balloon 40 can be passed using endovascular technique into the center section of the restrictor band 10 as shown in FIG. 7B. Once the balloon 40 is inflated to become an inflated balloon 45, the restrictor band 10 is stretched as shown in FIG. 7C. When the balloon is deflated as shown in FIG. 7D and removed, the restrictor band 10 maintains its expanded shape as shown in FIG. 7E. This system allows a narrowing to be established in the tube through which blood flows and then, if needed, remove the restriction to restore unrestricted blood flow. All this may occur with minimally invasive catheter and balloon techniques.

Figures 8A, 8B, 8C:
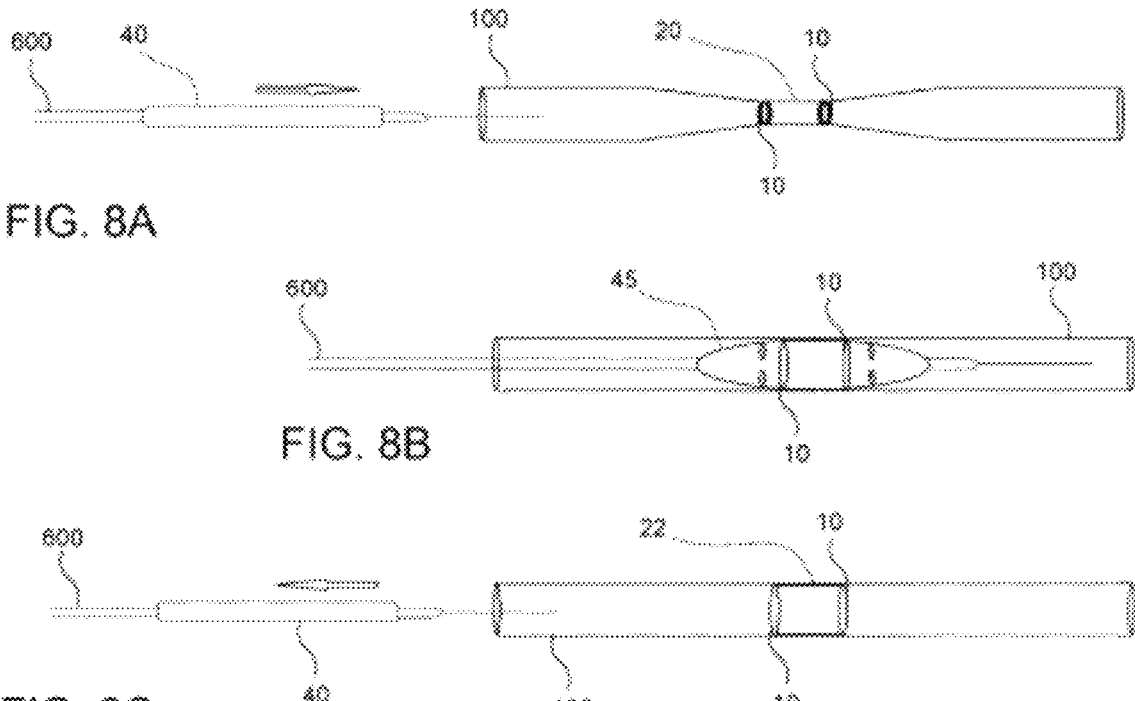
FIG. 8A is an illustration of a deflated balloon advancing into graft with long flow restrictor.
FIG. 8B is an illustration of an inflated balloon expanding long flow restrictor.
FIG. 8C is an illustration of a deflated balloon removal and expanded restrictor.

FIGS. 8A, 8B, and 8C illustrate a system and process as shown in FIGS. 7A-7E but with an expanded restricted area formed by two restrictor bands 10. As compared to FIGS. 7A-7E, similar elements are identified with identical reference numbers. In this embodiment, the expanded balloon 45 may have a wider area to expand both bands 10. This is similarly shown when the restrictor was initially deployed using the longer restrictor of FIGS. 8A through 8C. In a second embodiment, shown in FIGS. 9A through 9D, a fracturable restrictor band 10 is used, again creating a narrowing within the shunt. When a balloon is passed and inflated within the fracturable restrictor, the ring fractures at fracture points 700 as shown in FIG. 9B. Preset fracture points 700 break or fracture to allow the release of pressure and associated radial force existing within the tube 100, which were previously restrained by the fracturable restrictor band 10. Once fractured, the band is referred to as a fractured band 12. As shown in FIG. 9C, the balloon 40 is deflated for removal and the fractured band 12 no longer creates a stenosis. Then, in FIG. 9D, the shunt tube 100 is radially unrestricted. This allows expansion of the shunt tube 100, eliminating the narrow area and blood flow resistance. This creates a permanent loss of narrowing.

A third embodiment of the present invention is that of a resistor band 14 made of elastic materials. As shown in FIGS. 10A, 10B, 10C, 10D and 10E, the restrictor band 14 is created or deployed, and once the need arises to alter the restrictor band 14 it is temporarily opened. As shown in FIG. 10C, the balloon 45 is inflated to expand the restrictor band 14. This expands the stenosis and, based on the elasticity and properties of the restrictor band 14, the band may stay at a larger diameter for different periods of time. Once the balloon 40 is deflated, the elastic material of the restrictor band 14 reforms to its original state, again acting as a flow restrictor. The return to the narrow shape may occur rapidly or after a period of time. This may be useful when balloon angioplasty is needed in other parts of the shunt to help maintain patency, but the stenosis is still desired after the angioplasty. The elastic restrictor band 14 may be made of any material that is expandable and then returns to its narrowed diameter shape rapidly or slowly after expansion.

In one embodiment, the shunt is equipped with two or more fracturable restrictor bands such that one or more of the restrictor bands have a different diameter. In a basic embodiment, the first restrictor band has an inner diameter that is less than the inner diameter of the second restrictor band. Both are located around the outer surface of the shunt. In use, the shunt is placed in a patient which establishes a restriction or stenosis in the shunt, thereby reducing blood flow. If, over time, it is determined that the restriction is too great, then a balloon may be directed through a blood vessel to the shunt and filled with gas or liquid to increase the diameter of the balloon. The diameter of the balloon may be increased sufficiently to fracture the first restrictor band, while leaving the second restrictor band unaffected. Thus, after fracturing the first restrictor band, the inner diameter of the opening is increased to the diameter of the second restrictor band. If the doctor again determines the blood flow restriction is too great, then a balloon may be inserted inside the second restrictor to fracture the second restrictor band thereby again increasing the inner diameter of the shunt. This may occur with more than two restrictor bands to create additional degrees of control over the restriction size.

FIG. 11 illustrates one such embodiment that includes a stent tube having multiple bands of various diameters. This is but one possible configuration and as such other embodiments and configurations are possible, that which do not depart from the claims that follow. In this embodiment the shunt tube 100 includes an intake end configured to accept blood flow 824 as shown by the arrow. Any number of bands are possible but in this embodiment four bands 810, 814, 816, 820 are shown. A first band 810 has the smallest diameter, referred to herein as a first diameter. A second band 814 has a diameter greater than the first band 810, referred to herein as a second diameter. A third band 816 has a diameter greater than the second band 814, referred to herein as a third diameter. A fourth band 820 has a diameter greater than the third band 816, referred to herein as a fourth diameter.

In operation, a balloon (not shown) or other expansion device, may be inserted into the tube 100 and expanded sufficiently to fracture or otherwise expand the first band 810 thereby changing the diameter of the stenosis from the first diameter to the second diameter. If that stenosis is too small, then the process can be repeated at a later time to break the second band 814. This process may repeat to provide adjustability in the amount of narrowing in the stenosis including no narrowing by breaking all bands.

FIG. 12 illustrates an embodiment with a mirror set of bands. The first set of bands 1204A is duplicated with a second set of bands 1204B. The bands may be separated by a separation distance 1208B. Operation of this embodiment is as described above. The number of bands may vary from embodiment to embodiment. The value of the separation distance 1208B may vary to control blood flow dynamics as described herein. As the bands 1212 are broken, expanded, stretched, or separated, the tube will expand outward to a diameter determined by the band of the smallest diameter.

FIG. 13 illustrates an embodiment with bands having a greater width. It is also contemplated that the length of the stenosis may be determined by the width of the band. As such, the bands may be of different thickness or width. As shown in FIG. 13, the bands 1304 shown in cross section, are wider than those shown in the other embodiments. Varying the stenosis length will adjust blood flow dynamics. As with the other embodiments shown and described herein, the bands may be expanded to adjust the diameter of the stenosis. It is also contemplated that the width of each band may vary even for a single shunt tube 100. Thus, one band may be narrow, the next band wide, and the next band wider. Thus, each band would establish a different stenosis length.

FIG. 14A illustrates an implementation of tubular grafts 7000 of the present invention with an elastic flow restrictor 7500 having two tapered segments "a" and a central elastic restrictor segment "b", and configured with the tubular grafts coupled to and extending outwardly from a corresponding end of the tapered segments "a". As shown, the first and second tubular tubular grafts 7000 each have corresponding distal ends that are configured to be connected, directly or indirectly, to a corresponding one of an artery of a patient and a vein of a patient.

The length of the central elastic restrictor segment "b" can range, for example, from 0.5 mm to 30 mm, with the greater length providing the greatest decrease in resistance to blood flow. The diameter of the lumen of the central elastic restrictor segment can also be selected for a desired decrease in resistance to blood flow, and can vary, for example, from 2 mm to 4 mm. These dimensions can be selected by the clinician in consideration of factors such as cardiac output, patient average blood pressure and blood vessel sizes. The gender and race of a patient can also influence the desired parameters, as these factors have also been shown to be determinants in graft flow and patency. The lengths of tapered segments "a" will vary with the diameter of the central restrictor segment "b", and typically may range from 0.5 mm to 25 mm. The thickness of the wall of the elastic flow restrictor and graft, which affect the kinking properties of the graft, may range typically from 0.2 mm to 2.5 mm, with greater wall thicknesses being used for grafts of greater diameter. The elastic flow restrictor 7500 may be formed as a portion of the graft 7000 which is elastic, that is, the segments a and b can be expanded to a larger diameter approaching or matching that of the diameter of the graft 7000. The expansion is caused by a radially applied pressure from within the graft, such as that produced by a balloon catheter inside the elastic flow restrictor. When such pressure is applied, the elastic flow restrictor is expanded, and when such pressure is removed the elastic flow restrictor returns to its original configuration, either immediately or over time, i.e., the restrictor material has a relatively short or relatively longer relaxation time constant. The elastic flow restrictor 7500 may also comprise an elastic structural framework within or around the elastic flow restrictor that maintains the desired shape of the elastic flow restrictor when it is not subject to expansive pressure.

In the illustrated example of FIG. 14A the elastic structural framework comprises a series of rings integrated with the tapered segments and varying from a larger diameter to a smaller diameter over the length of the tapered segments. The structural framework can alternatively comprise a helical structures integrated with the two tapered segments. As the expansive pressure is applied to expand the central elastic restrictor segment b to a larger diameter, the structural framework of segments "a" follow, enabling the entire length of the elastic flow restrictor to be expanded to a larger diameter. The elastic structural framework may be made of various elastic materials which enable it to expand and contract, such as titanium or nitinol, the latter being a nickel-titanium alloy exhibiting a shape memory which enables the elastic flow restrictor to return to its original shape after being expanded. Other suitable materials include a cobalt-chromium-nickel alloy and stainless steel, a non-metallic material such as a polymer, nylon, and rubber.

FIG. 14B illustrates cross-sectional views of two implementations of elastic flow restrictor 7500. The first example illustrates a structural framework 7100 lined with a covering material 7250. In the second example a structural framework 7100 is lined with a covering material 7250 and is covered with an outer covering material 7200. The graft 7000 and its covering materials may be formed of ePTFE and attached to move with the structural framework and the rest of the elastic flow restrictor when it is expanded and retracts back to its original shape, and may utilize formation techniques such as adhesive bonding, wrapping, electrospinning, layering, or pre-sintered PTFE bead wrapping.

FIG. 15 illustrates another implementation of the present invention in which the central restrictor section "b" comprises an overlying elastic band 7700. This cylindrical design allows for a confluent diameter throughout the length of the central portion of the restrictor. FIG. 15A is a cross-sectional view showing the inner portion 7900 of the restriction surrounded by an outer cylindrical sleeve 7900. The elastic band 7700, 7900 may be formed of similar elastic materials as those of the elastic sections of the graft described above.

Figure 16A:
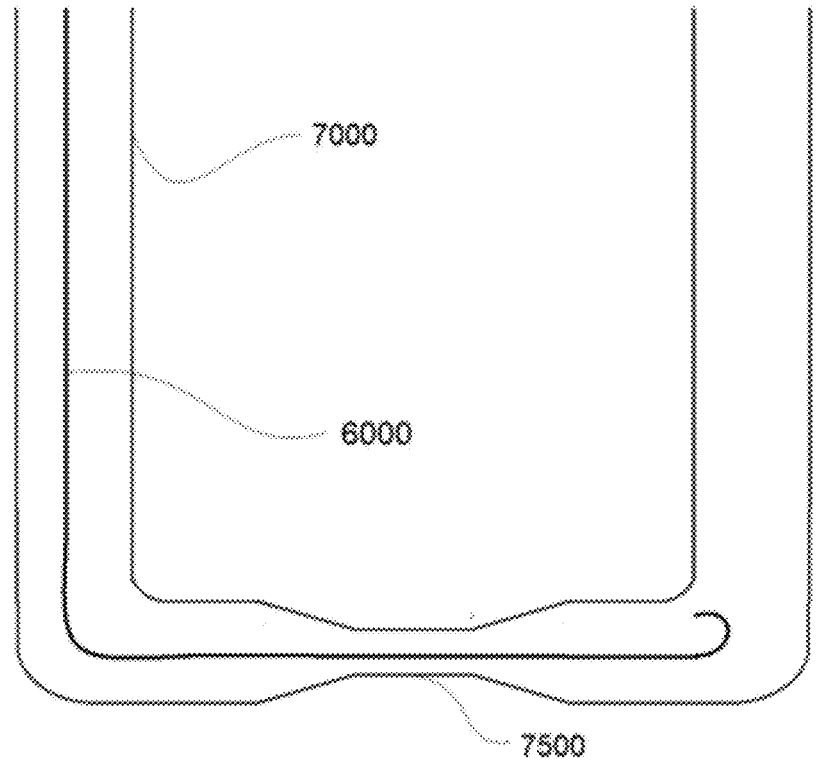
Figure 16B:
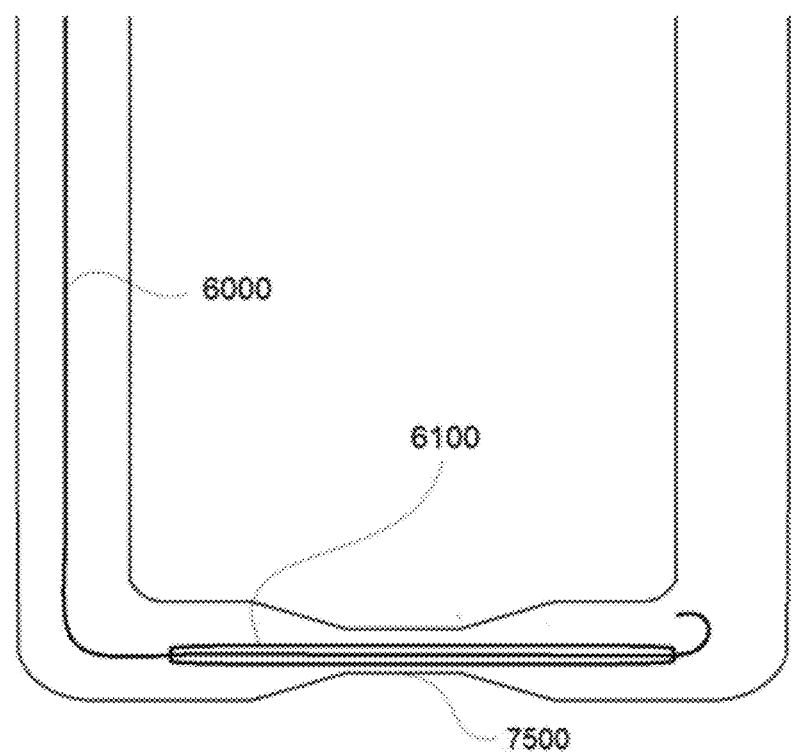
Figure 16C:
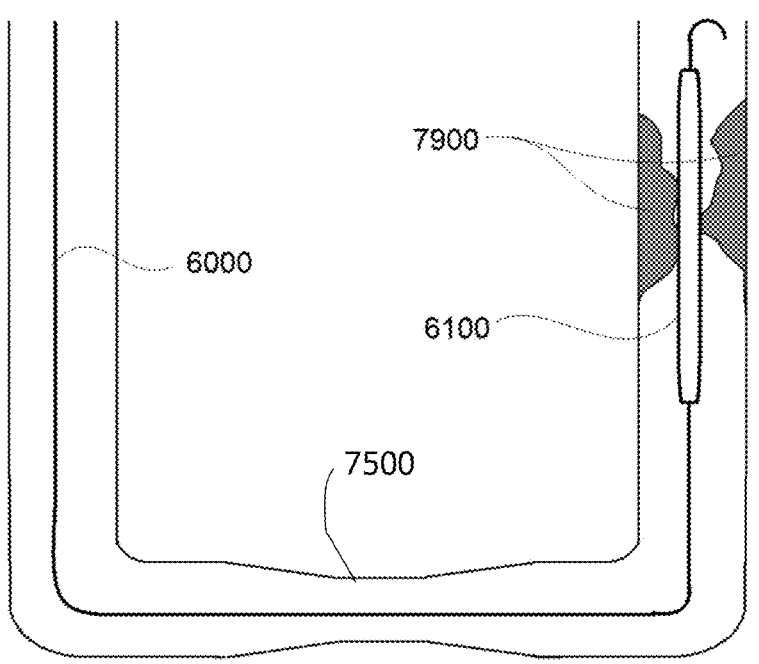
Figure 16D:
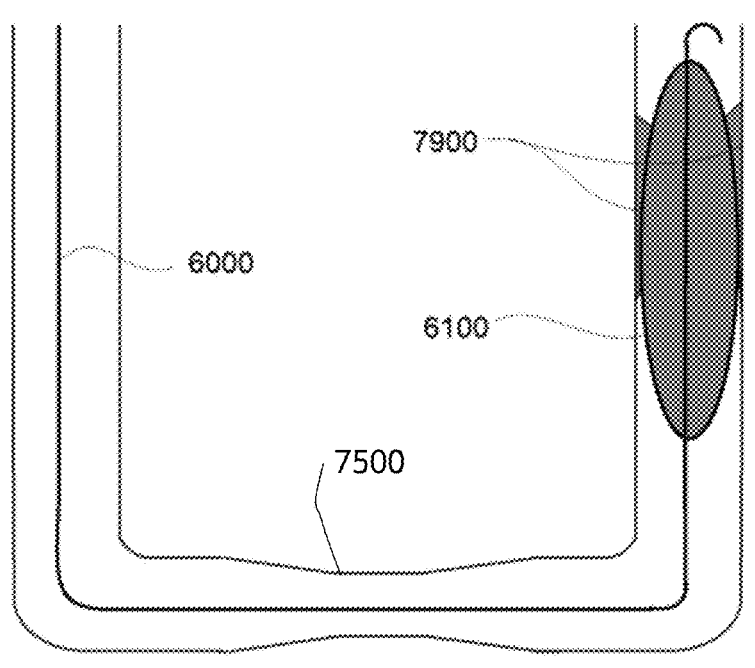
Figure 16E:
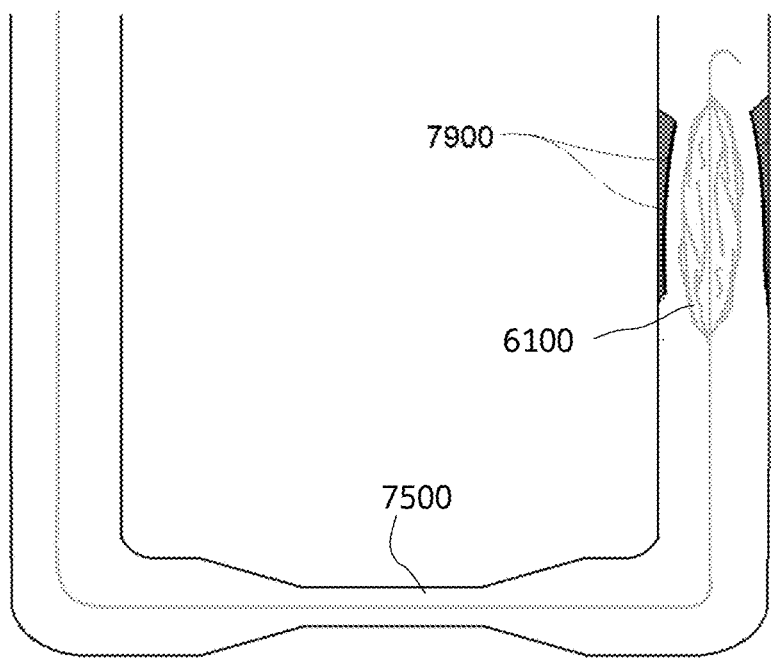

FIGS. 16A-16H illustrate the cleaning or rehabilitation of a graft of the present invention which comprises an elastic flow restrictor. This process is illustrated for grafts with two different elastic flow restrictors, one with material having a short relaxation time constant and another with material having a relatively long relaxation time constant. In FIG. 16A an endovascular guidewire 6000 is introduced into a graft 7000 and extends through an elastic flow restrictor 7500. In FIG. 16B an uninflated balloon 6100 is advanced over the wire and through the elastic flow restrictor 7500 toward the venous end of the graft. Since an uninflated packaged balloon is generally around 2 mm in diameter and a flow restrictor may be around 3 mm in diameter, the balloon 6100 can usually be advanced through the flow restrictor without distending it. FIG. 16C shows the balloon 6100 after its advance has continued through the graft until it opposes a plaque or blood clot obstruction 7900 in the venous end of the graft or in the vein to which it is attached. In FIG. 16D the angioplasty balloon 6100 has been inflated by standard hydrodynamic means to compress buildup on the wall of the graft and reopen the lumen of the graft. At the conclusion of the procedure, the angioplasty balloon is deflated as shown in FIG. 16E for withdrawal back through the elastic flow restrictor. However, the deflated balloon 6100 is no longer the size of the originally packaged balloon.

Figure 16F:
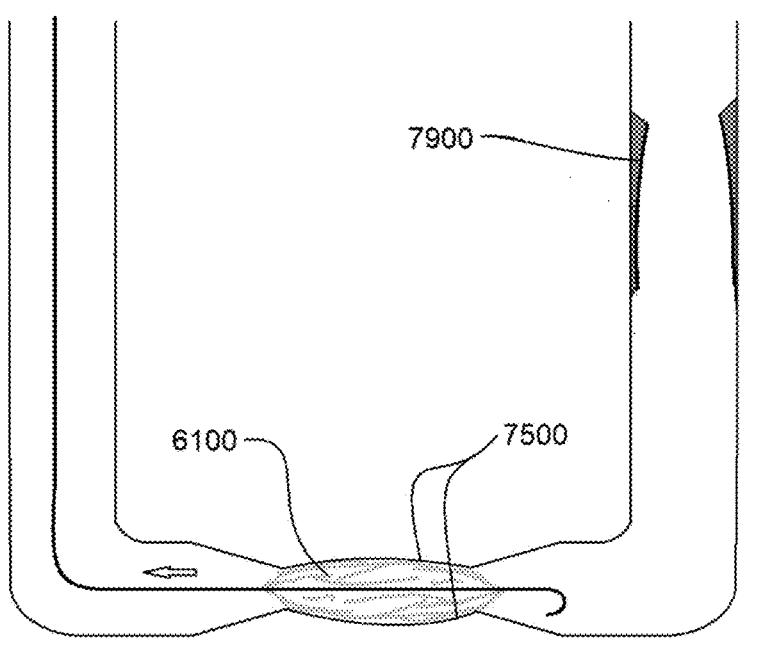
Figure 16G:
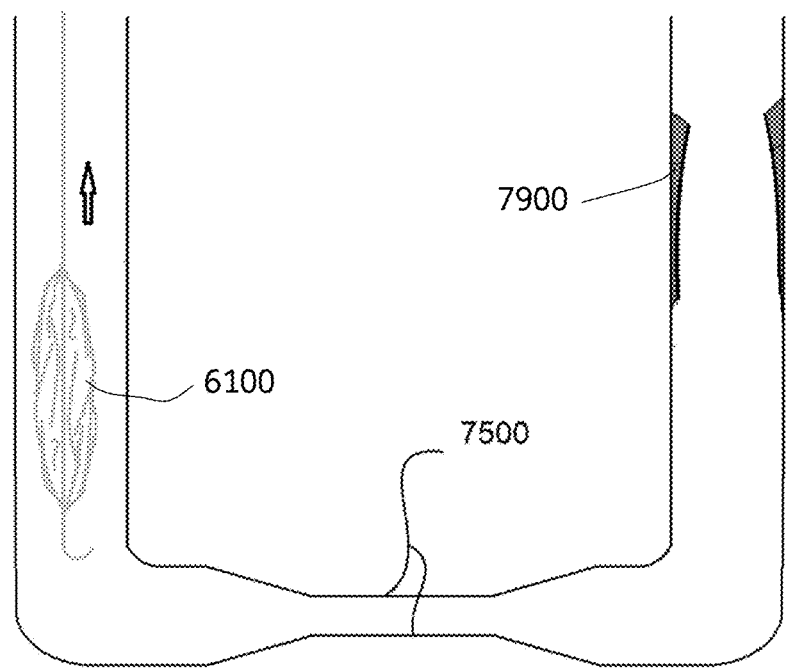

Consequently, as the balloon 6100 is pulled back, it will expand the elastic flow restrictor as it presses its way through, as illustrated in FIG. 16F. When the balloon 6100 is withdrawn further along the guidewire and exits the elastic flow restrictor lumen, the elastic flow restrictor quickly returns to its original configuration due to its relatively short relaxation time constant, as shown in FIG. 16G.

Figure 16H:
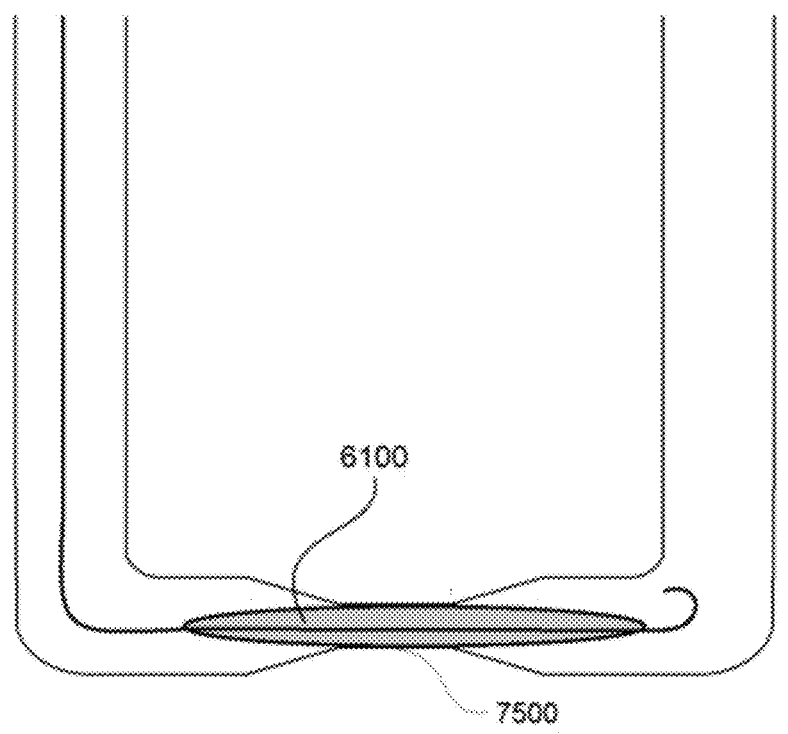
Figure 16I:
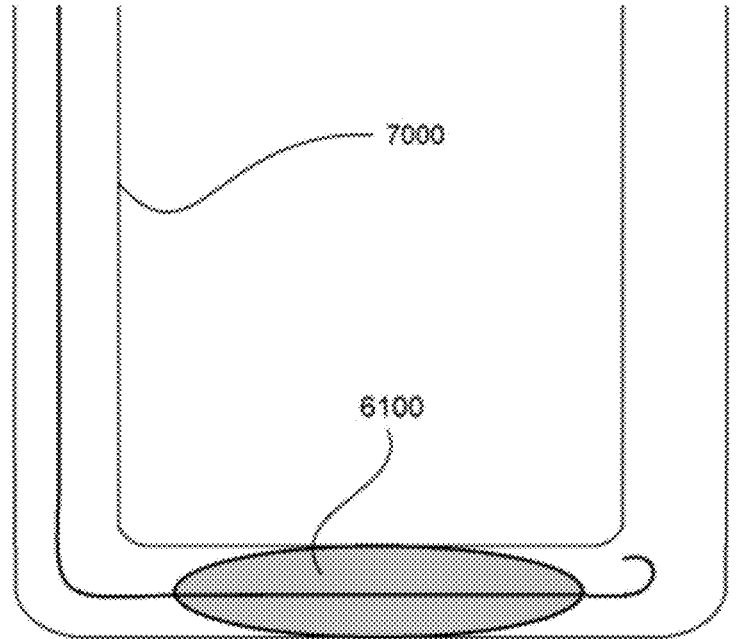
Figure 16J:
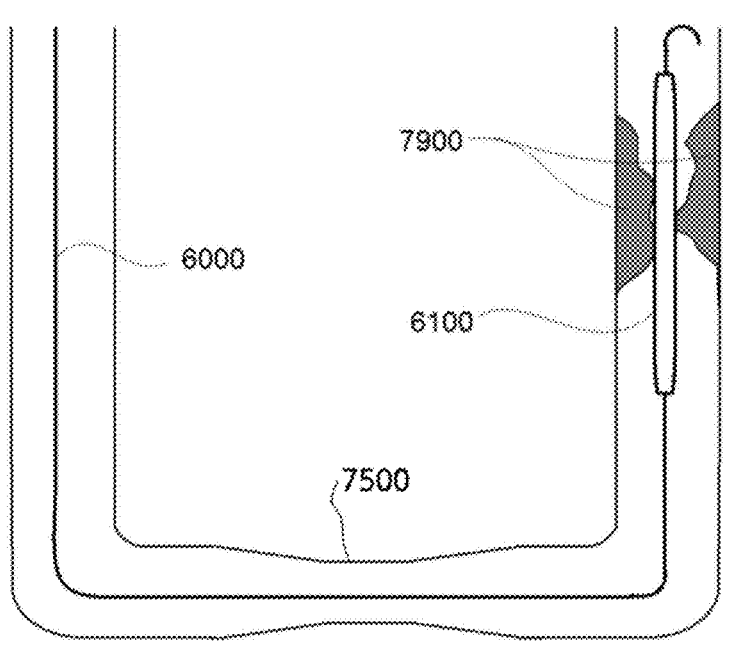
Figure 16K:
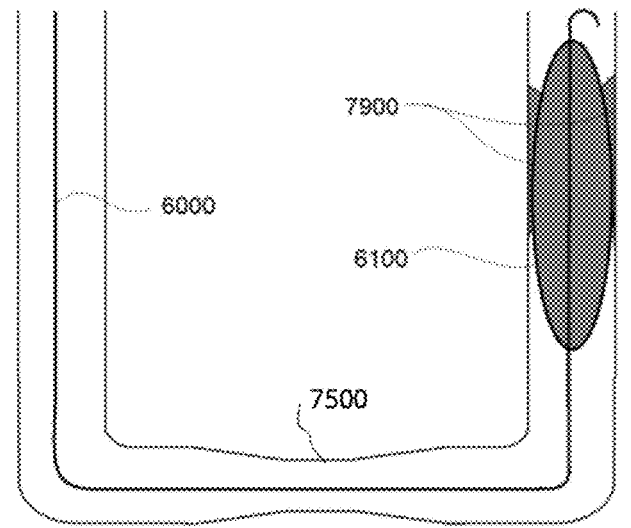

The drawings also illustrate how this procedure can be performed with an elastic flow restrictor exhibiting a relatively long relaxation time constant. Again the guidewire 6000 is advanced through the graft 7000 and through the elastic flow restrictor 7500 as shown in FIG. 16A. In FIG. 16B an uninflated balloon 6100 has advanced over the wire and is positioned within the elastic flow restrictor. FIG. 16H shows the balloon 6100 partially inflated and beginning to expand the elastic flow restrictor 7500, and FIG. 16I shows the balloon 6100 fully expanded and fully expanding the elastic flow restrictor. The balloon is then deflated and advanced through the graft 7000 until it opposes the plaque or clot buildup which is to be remedied, as shown in FIG. 16J. During this time and the remaining time of the procedure, the expanded elastic flow restrictor slowly begins to contract due to its relatively long relaxation time constant. In FIG. 16K the angioplasty balloon 6100 has been inflated to compress buildup on the wall of the graft and reopen the lumen of the graft. At the conclusion of the procedure, the angioplasty balloon is deflated and withdrawn back through the still-expanded elastic flow restrictor and out of the graft. In time, the continued contraction of the elastic flow restrictor will end when the restrictor has returned to its original configuration. It will be appreciated that when the elastic material used for the elastic flow restrictor exhibits a relatively long relaxation time constant, the restrictor may maintain a relatively expanded configuration for an appreciable period of time, during which tools may be advanced through the expanded stenosis, a procedure performed, and the tools withdrawn through the still-expanded flow restrictor before it has fully contracted to its original stenotic configuration.

FIGS. 17A-18B illustrate an implementation of the stent of FIGS. 4 and 5 in which the central restrictor segment "b" is formed of an elastic material. The central restrictor segment "b" has first and second opposing ends, as shown, and a central lumen extending therebetween and having a stenotic inner diameter when not subject to radially expansive pressure. As in the previous implementation, the tapered segments "a" are collapsible for insertion into the vascular system and expandable to affix the stent in a desired location in a blood vessel or graft. That is, the first and second tapered segments "a" are configured to expand when the stent is deployed into at least one of a fistula and a graft in order to retain the stent in a predetermined location therein. In one example, the first and second tapered segments "a" each have a central lumen and extend from a corresponding one of the first and second ends of the elastic central restrictor segment "b". The first and second tapered segments "a" also preferably have ends that are spaced from the elastic central restrictor segment "b", and are configured to have corresponding first and second diameters each configured to be greater than the stenotic inner diameter when the stent is in a predetermined use position (i.e., deployed in a patient during dialysis). Additionally, the first and second tapered segments "a" are also preferably configured to move radially in concert with movement of the first and second ends of the elastic central restrictor segment "b" to which they are attached. Moreover, the elastic central restrictor segment "b" is further configured to elastically expand radially when radially expansive pressure is applied in the central lumen of the elastic central restrictor segment "b", and to elastically contract to its stenotic inner diameter when the radially expansive pressure is removed.

FIG. 17A illustrates metallic collapsible and expandable tapered segments "a" of the stent on either side of a central elastic segment "b", denoted as elastic segment 8000. That is, the first and second tapered segments "a" are made of a first material (e.g., a metallic material) and the elastic central restrictor segment "b" is made of a second material different than the first material.

The tapered segments "a" also preferably have first and second diameters configured to be greater than the stenotic inner diameter of the central restrictor segment "b" when the stent is in a predetermined use position (i.e., deployed within a patient for use in dialysis). The elastic segment is made of the same materials as the central restrictor segments of the previous elastic restrictor implementations. FIG. 17B illustrates the stent of FIG. 17A with an outer covering 8100 of ePTFE or other material covering at least an exterior surface of each of the central elastic segment "b" and each of the tapered segments "a". In FIG. 18A the central elastic segment "b" is formed of an expandible structural framework covered by an outer elastic sleeve 8200. In this example, the elastic sleeve 8200 concentrically surrounds the central restrictor segment "b". In FIG. 18B a fully covered stent utilizes an outer elastic sleeve 8200 to maintain the central restrictor segment "b" in its stenotic configuration. In this example, the outer elastic sleeve 8200 concentrically surrounds the outer covering (not labeled in FIG. 18B, but see covering 8100 in FIG. 17B) at the central restrictor segment "b". Typical dimensions and materials may be the same as those described for the elastic flow restrictor of FIGS. 14 and 15.

It will also be appreciated that in each of the embodiments of FIGS. 17A-18B, the stents may further include at least a first structure and a second structure each integrated with a corresponding one of the first and second tapered segments "a" and being made of a material different than a material of the first and second tapered segments "a". These structures are configured to be similar to the elastic structural frameworks of FIG. 14A, discussed above. That is, the structures of the tapered segments "a" may include a first series of ring structures and a second series of ring structures each integrated with a corresponding one of the first and second tapered segments "a" and each varying from a first diameter to a second diameter smaller than the first diameter over a length of the corresponding one of the first and second tapered segments "a". The structures may also include first and second helical structures each integrated with a corresponding one of the first and second tapered segments "a".

FIG. 19 illustrates the deployment of a collapsible elastic dialysis stent 8000 with a central elastic restrictor segment of the present invention. In FIG. 19A the dialysis stent 8000 is fully collapsed and contained within a deployment sheath 2005, with the distal end of the sheath located at a desired location in a fistula or graft for placement of the stent. A pusher rod 2010 is advanced to the right (as indicated by the arrow at the left end of the sheath) and the sheath is moved to the left (as indicated by the arrow above the sheath) to eject the collapsed dialysis stent from the sheath. FIG. 19B shows the dialysis stent 8000 beginning to emerge from the sheath with its leading self-expanding tapered portion 8001 fully expanded. As the pusher rod continues to expel the dialysis stent from the sheath and the sheath continues to be withdrawn from the placement site, the central restrictor segment 8002 emerges from the sheath as illustrated in FIG.

19C. In FIG. 19D the dialysis stent has been fully ejected from the sheath, the sheath and pusher rod are withdrawn from the site, and the second self-expanding tapered portion has expanded to retain the stent in place in a graft or fistula.

That is, the stent 8000 is configured to be located in the sheath for deployment in a stowed configuration in which the first and second tapered segments "a" are collapsed, and responsive to separation between the stent 8000 and the sheath, the first and second diameters of the tapered segments "a" are configured to increase in a manner wherein the first diameter (in the example of FIG. 19, the first diameter corresponds to the tapered segment "a" on the right) increases before the second diameter. Additionally, also responsive to separation between the stent and the sheath, the stenotic inner diameter of the stent 8000 is configured to increase from a first stenotic inner diameter to a second stenotic inner diameter such that each of the first and second stenotic inner diameters are less than the first and second diameters of the first and second tapered segments "a" after the stent has been separated from the sheath. In other words, the central restrictor segment "b" has to collapse at least a predetermined amount in order to be received in the sheath, and as such expands to a greater diameter upon being separated from the sheath.

FIG. 20 illustrates the covered elastic dialysis stent 8100 of FIG. 17B with its central elastic segment, tapered end segments, and covering material. The series of steps depicted in FIG. 20 show the stent being expanded by a balloon catheter and thereafter elastically contracting to its original stenotic fluid passageway configuration after the balloon catheter is deflated and withdrawn. In FIG. 20A a guidewire 2500 accesses the dialysis stent 8100 and passes through its central restrictor segment. In FIG. 20B an uninflated balloon catheter 2550 is advanced over the guidewire and approaches the dialysis stent. In FIG. 20C the balloon has advanced to the center of the dialysis stent. In FIG. 20D the balloon is shown partially inflated and the elastic dialysis stent has partially expanded diametrically. In FIG. 20E the balloon 2550 is seen fully expanded and the elastic dialysis stent is also fully expanded in diameter. FIG. 20F shows the elastic reformation of the stent 8100 to its original dimensions following deflation of the balloon catheter.

Put differently, responsive to a balloon catheter being introduced into the central lumen of the elastic central restrictor element by the guidewire, and subsequently radially expanded, the lumen of the elastic central restrictor element "b" is configured to expand to a predetermined dimension in order to allow an endovascular medical device to pass through the lumen. Additionally, the lumen of the elastic central restrictor segment "b" is configured to receive the endovascular medical device in order to allow stent repair to be performed in a venous graft segment or vein.

FIG. 21 is similar to FIG. 20 and depicts an elastic dialysis stent of the present invention with an elastic sleeve 8200 providing the stenotic formation of the central restrictor segment of the stent. As in the previous drawing a guidewire 2500 is passed through the stent (FIG. 21A) and a balloon catheter 2550 is advanced over the guidewire (FIG. 21B) until it is positioned in the center of the stent (FIG. 21C). In FIG. 21D the balloon catheter is partially inflated and the elastic stent and sleeve are partially expanded, and in FIG. 21E the balloon 2550 is fully inflated and the elastic stent and sleeve are fully expanded. In FIG. 21F the balloon catheter is shown deflated and the elastic stent and sleeve have elastically returned to their original configuration.

Following a reading of the foregoing explanations and analysis, variations of implementations of the present invention may readily occur to those skilled in the art. For instance, while the tapered segments "a" of a stent are shown in the drawings as a progressive narrowing of the lumens of such segments over a length of the stent, implementations of the present invention can also exhibit relatively rapid tapering, including those in which the diameter of the lumen of the stent is sharply reduced from a large lumen to a smaller lumen in an instantaneous reduction of lumen diameter.

The invention claimed is:

1. A hemodialysis access method for a patient, comprising:

deploying a dialysis stent within an arterial venous (AV) fistula or graft, the dialysis stent having an expandable restriction and comprising a shunt tube and at least one elastic restrictor, the shunt tube having an inlet end, an outlet end, and a central opening extending from the inlet end to the outlet end such that the central opening has a first diameter, the at least one elastic restrictor extending around a portion of the shunt tube located between the inlet end and the outlet end, the at least one elastic restrictor narrowing the central opening in order to create a stenosis in the shunt tube that acts as a flow restrictor for allowing the shunt tube to elastically shunt blood flow from an extremity of the patient, and in order to create a reduced diameter section of a second diameter in the shunt tube that is elastically adjustable from the second diameter, which is less than the first diameter, to a third diameter that is greater than the second diameter such that the stenosis expands when the shunt tube moves from having the second diameter to having the third diameter; and elastically adjusting the at least one elastic restrictor from the second diameter to the third diameter responsive to a balloon inflating to expand the at least one elastic restrictor, and from the third diameter back to the second diameter responsive to the balloon subsequently deflating.

2. The method according to claim 1, further comprising elastically reforming the at least one elastic restrictor from an expanded state to an original state when adjusting from the third diameter back to the second diameter.

3. The method according to claim 2, further comprising exerting radial pressure on the shunt tube by the at least one elastic restrictor both when the shunt tube has the second diameter and when the shunt tube has the third diameter.

4. The method according to claim 3, further comprising providing an elastic material of the at least one elastic restrictor as being different than a material of the shunt tube in order to create a radially inward pressure on the shunt tube and to allow the shunt tube to have smooth inner and outer surfaces proximate the at least one elastic restrictor.

5. The method according to claim 3, further comprising providing the at least one elastic restrictor as having a first thickness greater than a second thickness of the shunt tube in order to create a radially inward pressure on the shunt tube and to allow the shunt tube to have smooth inner and outer surfaces proximate the at least one elastic restrictor.

6. The method according to claim 3, wherein the at least one elastic restrictor comprises an elastic band.

7. The method according to claim 3, wherein the at least one elastic restrictor comprises an elastic covering material.

8. The method according to claim 3, being performed without folding of the at least one elastic restrictor.

9. The method according to claim 3, wherein the third diameter is the same as the first diameter.

10. The method according to claim 3, wherein the at least one elastic restrictor is expandable from the third diameter to a fourth diameter, and wherein the fourth diameter is greater than the third diameter.

11. The method according to claim 3, wherein elastically adjusting is performed without an additional medical procedure in a manner wherein the at least one elastic restrictor is a sole force for radially contracting the shunt tube back to the second diameter.

12. The method according to claim 3, further comprising providing each of the shunt tube and the at least one elastic restrictor with a middle disposed midway between the inlet and outlet ends of the shunt tube.

13. The method according to claim 3, further comprising connecting an artery of the patient to a vein of the patient with the AV fistula or graft before deploying the dialysis stent within the AV fistula or graft, wherein elastically adjusting further comprises radially expanding the shunt tube outwardly when the shunt tube adjusts from the second diameter to the third diameter.

14. The method according to claim 1, further comprising:
  providing the shunt tube with an elastic central restrictor segment, and a first tapered segment and a second tapered segment each having a central lumen and extending from a corresponding end of the elastic central restrictor segment;
  providing each of the first and second tapered segments with a corresponding end spaced from the elastic central restrictor segment, the corresponding end having a corresponding diameter configured to be greater than the first diameter and the second diameter; and
  moving the first and second tapered segments radially in concert with movement of the corresponding end of the elastic central restrictor segment to which they are attached.

15. The method according to claim 14, further comprising:
  elastically expanding the elastic central restrictor segment radially when radially expansive pressure is applied within the elastic central restrictor segment; and
  elastically contracting the elastic central restrictor segment to the second diameter when the radially expansive pressure is removed.

16. The method according to claim 14, further comprising providing the first and second tapered segments as being made of a first material and the elastic central restrictor segment as being made of a second material different than the first material.

17. The method according to claim 16, further comprising providing the first material as being a metallic material.

18. The method according to claim 14, further comprising providing an outer covering for covering at least an exterior surface of each of the central elastic segment and each of the first and second tapered segments.

19. The method according to claim 14, further comprising concentrically surrounding the outer covering at the elastic central restrictor segment with an elastic sleeve for maintaining a stenotic configuration of the dialysis stent.

20. The method according to claim 14, further comprising receiving within the elastic central restrictor segment an endovascular medical device in order to allow stent repair to be performed in the AV fistula or graft.

21. The method according to claim 14, further comprising integrating at least a first structure and a second structure with a corresponding one of the first and second tapered segments, wherein the first and second structures are each made of a material different than a material of the first and second tapered segments.

22. The method according to claim 14, further comprising expanding each of the first and second tapered segments when the dialysis stent is deployed within the AV fistula or graft in order to retain the dialysis stent in a predetermined location therein.

23. The method according to claim 1, further comprising providing the at least one elastic restrictor with a structural framework and a covering material lining the structural framework, wherein the covering material is configured to move with the structural framework when the at least one elastic restrictor is elastically adjusted in order to elastically shunt the blood flow from the extremity of the patient.

24. The method according to claim 23, further comprising providing the covering material as being lined on an inside of the structural framework.

25. The method according to claim 24, further comprising providing another covering material lining an outside of the structural framework, wherein the another covering material is configured to move with the structural framework when the at least one elastic restrictor is elastically adjusted in order to elastically shunt the blood flow from the extremity of the patient.

* * * * *